(12) United States Patent
Su

(10) Patent No.: US 8,498,824 B2
(45) Date of Patent: Jul. 30, 2013

(54) NUCLEIC ACID SEQUENCING USING A COMPACTED CODING TECHNIQUE

(75) Inventor: Xing Su, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 442 days.

(21) Appl. No.: 12/131,918

(22) Filed: Jun. 2, 2008

(65) Prior Publication Data

US 2009/0298702 A1    Dec. 3, 2009

(51) Int. Cl.
*G06F 19/28* (2011.01)
*H03M 7/00* (2006.01)
*G06F 19/22* (2011.01)
*G07F 7/00* (2006.01)

(52) U.S. Cl.
USPC ............................... 702/20; 341/55; 341/106

(58) Field of Classification Search
None
See application file for complete search history.

(56) References Cited

U.S. PATENT DOCUMENTS 7,769,729 B2 * 8/2010 Faerber et al. ................ 707/693
2004/0086861 A1 * 5/2004 Omori ............................ 702/20

FOREIGN PATENT DOCUMENTS

WO    WO 99/01940    *    1/1999

OTHER PUBLICATIONS

Liu (Dec. 12, 2003) Bioinformatics vol. 19 pp. 2397 to 2403.*
Huang (Dec. 16, 2006) Nucleic Acids Research vol. 35 pp. 678 to 686.*
Grumbach (Apr. 2, 1993) IEEE the Proceedings of the Data Compression Conference pp. 340 to 350.*
Chen, X., Li, M., Ma, B. & Tromp, J. DNACompress: fast and effective DNA sequence compression. Bioinformatics 18, 1696-1698 (2002).*
Matsumoto, T., Sadakane, K. & Imai, H. Biological sequence compression algorithms. Workshop on Genome Informatics 11, 43-52 (2000).*

* cited by examiner

*Primary Examiner* — Soren Harward
(74) *Attorney, Agent, or Firm* — Trop, Pruner & Hu, P.C.

(57) ABSTRACT

Methods and apparatuses for nucleic aced sequencing using a compacted code technique are disclosed. In one embodiment, a method includes providing a nucleic acid to be sequenced, determining the identity of each base in a subsequence of bases in the nucleic acid, encoding the identity of the subsequence in a format having a number of bytes that is less than the number of bases, and storing the encoded identity.

3 Claims, 3 Drawing Sheets

METHOD 100

METHOD 300

NUCLEIC ACID SEQUENCING USING A COMPACTED CODING TECHNIQUE

BACKGROUND

1. Field

The present disclosure pertains to the fields of genomics and molecular biology, and, more specifically, to the field of nucleic acid sequencing.

2. Description of Related Art

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides, which are in turn made up of a sugar (deoxyribose or ribose, respectively), phosphoric acid, and one of four bases, adenine (A), cytosine (C), guanine (G), and thymine (T) or uracil (U).

The human genome, for example, contains approximately three billion nucleotides of DNA sequence. DNA sequence information can be used to determine genetic characteristics of an individual, including the presence of and or suceptibility to many common diseases, such as cancer, cystic fibrosis, and sickle cell anemia. Determination of the entire three billion nucleotide sequence of the human genome has provided a foundation for identifying the genetic basis of such diseases. A determination of the sequence of the human genome required years to accomplish. Sequencing the genomes of individuals provides an opportunity to personalize medical treatments. The need for nucleic acid sequence information also exists in clinical applications, such as for example, pathogen detection (the detection of the presence or absence of pathogens or their genetic variants), and in research in environmental protection, food safety, bio-defense, and other areas.

A typical method for nucleic acid sequencing involves producing many copies of a gene, cutting it into overlapping fragments, determining the sequences of individual fragments, collecting the data, and analyzing the data to assemble the sequences of the individual fragments into the sequence of the gene. Due to the large amount of data required to sequence genes and other functional units of DNA, the data analysis and assembly might be performed as a separate process, only after many separate sequencing processes have been completed.

BRIEF DESCRIPTION OF THE FIGURES

The present invention is illustrated by way of example and not limitation in the accompanying figures.

DETAILED DESCRIPTION

The following description describes embodiments of techniques for nucleic acid sequencing using a compacted coding technique. In the following description, specific details may be set forth in order to provide a more thorough understanding of the present invention. It will be appreciated, however, by one skilled in the art that the invention may be practiced without such specific details. Additionally, some well known information has not been described in detail, to avoid unnecessarily obscuring the present invention.

Embodiments of the present invention provide for nucleic acid sequencing using a compacted coding technique. Using embodiments of the present invention may be desirable to reduce the volume of collected data, so as to facilitate the analysis and assembly of sequencing data while the sequencing of fragments is still in progress, rather than after the fragment sequencing has been completed. Therefore, more rapid, more efficient, and less costly nucleic acid sequencing may be possible.

Figure 1:
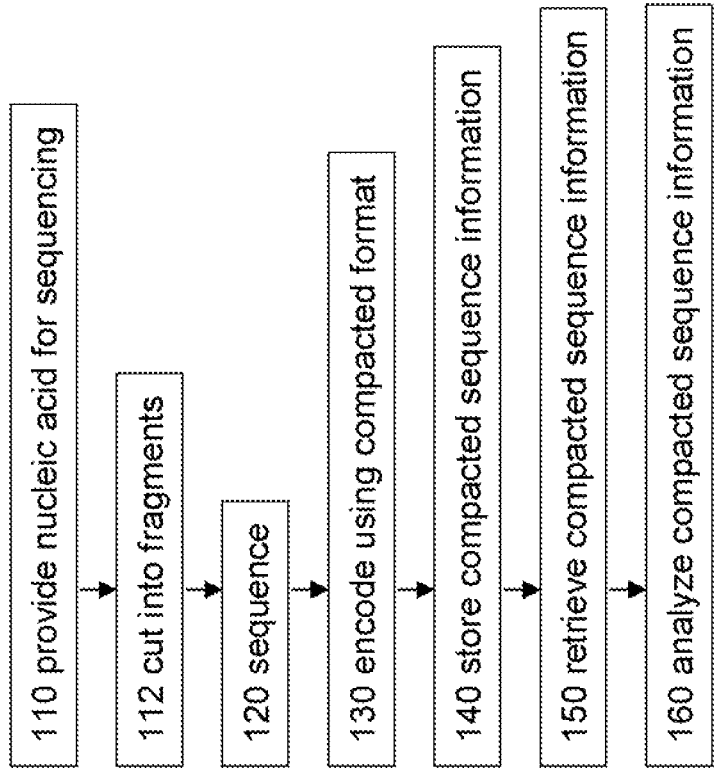
FIG. 1 illustrates an embodiment of the invention in a method for nucleic acid sequencing using a compacted coding technique.

FIG. 1 illustrates an embodiment of the invention in a method for nucleic acid sequencing. In block 110 of method 100, several copies of a nucleic acid to be sequenced, such as a DNA or RNA molecule, are provided. In block 112, the copies are cut into overlapping fragments, according to any known technique.

In block 120, sequencing is performing, according to any known technique, to determine the identity of each base in one or more subsequences in one or more of the fragments. Each base is identified using a code in which the identity of each base is represented by a value having a size of one byte (i.e., eight bits). For example, the code may be the typical code used to encode each of a set of alpha-numeric characters as one unique byte, where adenine may be represented using the byte value for the letter A, cytosine may be represented using the byte value for the letter C, guanine may be represented using the byte value for the letter G, and thymine may be represented using the byte value for the letter T. Therefore, in one embodiment, a subsequence of ten bases may be encoded as a series of ten bytes. Such a coding technique, in which the number of bytes of data used to represent a subsequence of bases equals the number of bases in the subsequence, may be referred to as uncompacted coding technique, in contrast to a compacted coding technique, as will be described next.

In block 130, the identification of one or more of the subsequences found in block 120 may be encoded using a compacted coding technique, where a compacted coding technique is one in which the number of bytes of data used to represent a subsequence of bases is less than the number of bases in the subsequence. For example, for a subsequence of ten bases, where each base may be one of either A, C, G, or T, there may be a total of $4^{10}$, or 1,048,576, unique subsequences. In one embodiment, a seven-digit decimal value, e.g., ranging from 1 to 1,048,576, is assigned to each unique subsequence. In this embodiment, one byte is used for each digit of the decimal value, so the identification for a ten base subsequence may be represented using seven bytes.

In other embodiments, other compacted coding techniques may be used. For example, each of the 1,048,576 unique subsequences described above may be encoded as a unique 20-bit value. As another example, where a fifth alphanumeric value, e.g., N, is used to represent a base with an unknown or unneeded identity, there may be a total of $5^{10}$, or 9,765,625, unique subsequences, and each may be encoded with one byte per digit of a seven-digit decimal value.

In block 140, compacted identifiers of subsequences are stored in a memory. By storing compacted identifiers rather than uncompacted identifiers, less memory space is required, and subsequent use of the data in comparisons and other computations for assembly and other analysis may be more efficient.

In block 150, one or more encoded subsequences are retrieved from the memory. In block 160, one of the encoded subsequences, either directly from block 130 (i.e., not retrieved from memory) or retrieved from memory in block 150, of a fragment is compared to an encoded subsequence, either directly from block 130 (i.e., not retrieved from memory) or retrieved from memory in block 150, in another fragment. Each of these two subsequences may be at an end of the fragment that it is in, such that if the two subsequences match, the sequences (whether completely determined yet or not) of the two fragments may be assembled to determine a sequence of a portion of the nucleic acid that is longer than the sequence of either individual fragment.

Blocks 120, 130, 140, 150, and 160 may be performed according to a parallel or overlapping approach. For example, a ten-base subsequence in a fragment may be sequenced in block 120. Then, in block 130, the ten-base subsequence may be encoded in the compacted format while one or more of the next bases in the same fragment are identified in block 120. Meanwhile, in block 160, completed encodings of other subsequences in the same or another fragment may be compared to subsequences in other fragments. Therefore, assembly and sequencing may be performed together, rather than as two separate processes.

In some embodiments, more than one compacted code may be used together. For example, ten-base subsequences at an end of a fragment may be encoded in the seven-byte code described above, and ten-base subsequences that are not at the end of a fragment may be encoded as a single byte, e.g., the character N, to represent a subsequence for which the complete information is not known or not needed. Such may be the case because the fragments may be initially assembled by comparing only the ends of fragments to each other. For example, 90-base sequences may be encoded in 21 bytes, starting with a seven-byte value to provide the complete sequence of the first ten bases, followed by seven bytes, each with a value of N, to represent the next 70 bases, followed by another seven-byte value to provide the complete sequence of the last ten bases. Although each 21-byte value does not provide complete or unique identification information, the storage and data analysis requirements may be greatly reduced, as a 21-byte value may be used to represent one of $4^{90}$, or $1.5 \times 10^{54}$, possible sequences.

Within the scope of the present invention, method 100 may be performed in a different order, with illustrated block performed simultaneously, with illustrated blocks omitted, with additional blocks added, or with a combination of reordered, combined, omitted, or additional blocks.

Figure 2:
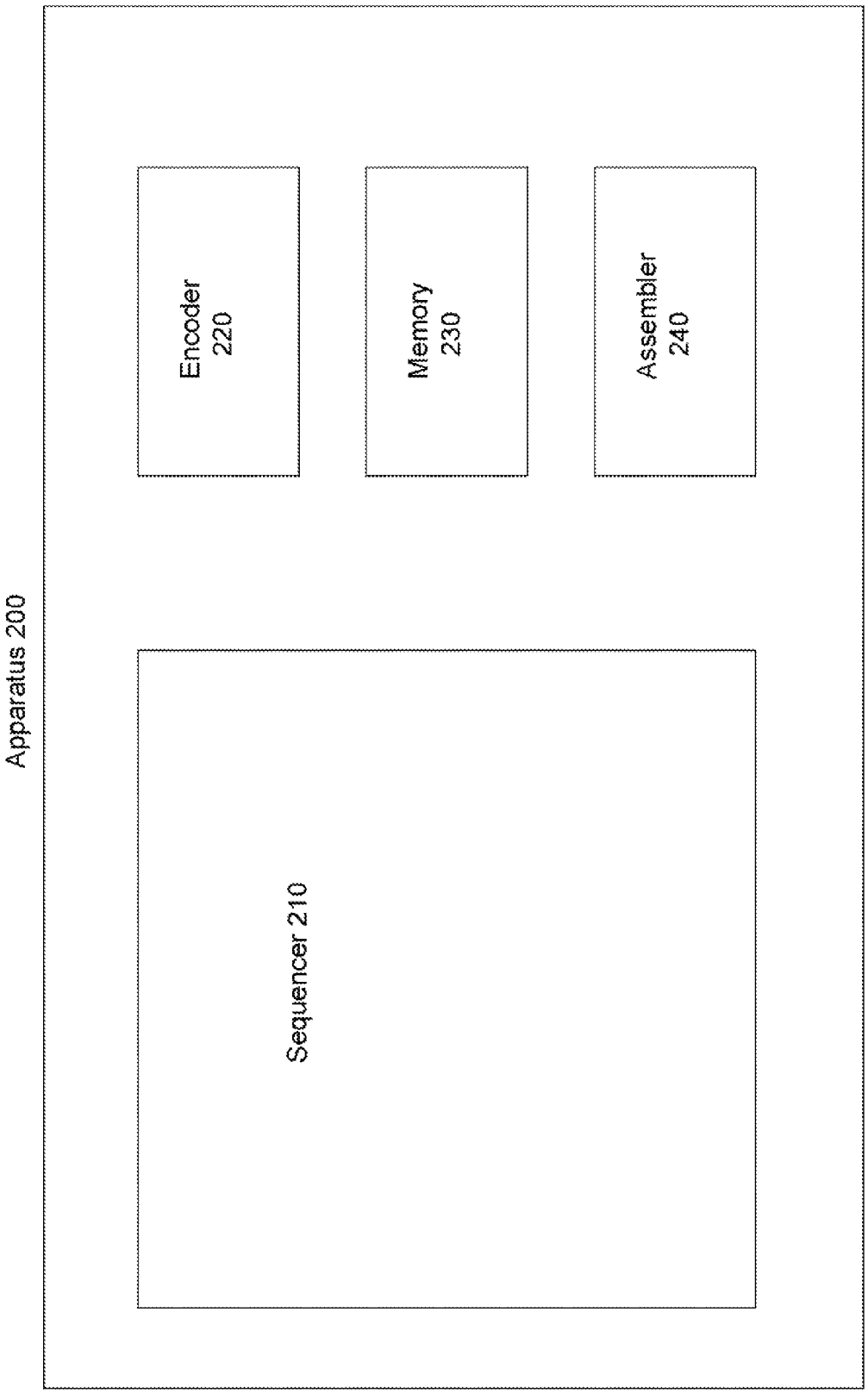
FIG. 2 illustrates an embodiment of the invention in an apparatus for nucleic acid sequencing using a compacted coding technique.

FIG. 2 illustrates an apparatus for nucleic acid sequencing using a compacted encoding technique according to an embodiment of the present invention. Apparatus 200 includes sequencer 210, encoder 220, memory 230, and assembler 240. Embodiments of the present invention may provide for an apparatus 200 that performs nucleic acid sequencing and assembly in parallel or according to an overlapping approach, as described above, and/or using a substrate onto which the sequencing and assembly functions are integrated, such as a silicon or other semiconductor-based integrated circuit.

Sequencer 210 may include a silicon-based high density electrochemical sensor array, or any other hardware for identifying bases in nucleic acid fragments according to any known approach. Encoder 220 may include any circuitry or logic for encoding subsequences of bases identified by sequencer 210 in a compacted code, as described above with reference to FIG. 1. Memory 230 may include any storage medium readable by assembler 240, such as semiconductor-based static or dynamic random access memory, to store encoded sequence information generated by encoder 220 or obtained from any other source. Assembler 240 may include any circuitry or logic to compare, or otherwise analyze, and assemble encoded subsequence information generated by encoder 220 and/or retrieved from memory 230.

Figure 3:
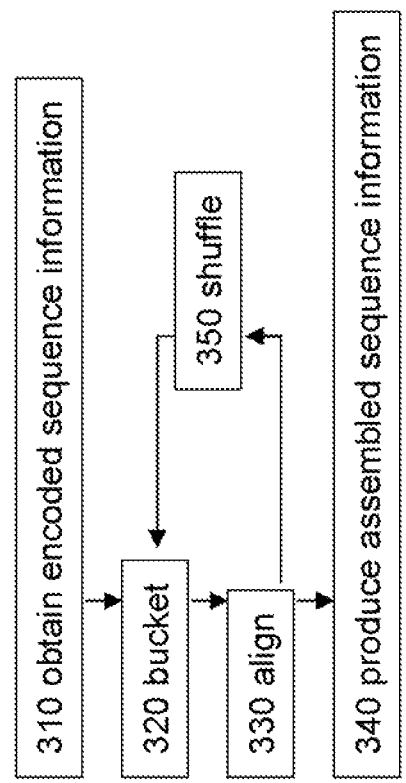
FIG. 3 illustrates an embodiment of the invention in a method for nucleic acid sequencing using a high density sensor array on which many fragments may be sequenced in parallel.

FIG. 3 illustrates an embodiment of the invention in a method for nucleic acid sequencing using a high density sensor array on which many fragments may be sequenced in parallel.

In block 310 of method 300, sequence information using a compacted code is obtained from each array location. In block 320, the sequence information is grouped, or "bucketed," such that the sequence information from a first subset of array locations is assigned to a first group, or "bucket," the sequence information from a second subset of array locations is assigned to a second bucket, and so on. In block 330, the sequence information within each bucket is compared or otherwise analyzed to align or assemble fragments within each bucket, and yield possible and/or true partially assembled sequences in block 340. In block 350, the sequence information is regrouped, or "shuffled," such that block 320 may be repeated with at least one array location being assigned to a different bucket than it was assigned to in the previous iteration of block 320.

The shuffling, bucketing, and alignment of method 300 may be repeated multiple times, to yield more and more assembled sequence information as sequencing of fragments progresses. Therefore, fragments may be matched and aligned with each other and/or to known sequence information based on partial or incomplete sequence information, to yield possible positions for fragments with respect to each other and/or to known sequence information, and be proven true or false as sequencing progresses. In one embodiment, this includes initially comparing and matching fragments based on subsequences at the ends of fragments, which may be coded with more complete information than the subsequences not at the ends of fragments, as described above, then confirming possible matches, by incrementally extending the sequence information, comparisons, and matching away the ends of the fragments.

Thus, techniques of the present invention may be used to reduce the volume of data and the computation time needed for nucleic acid sequencing and assembly, and may make real-time sequencing and assembly possible.

Embodiments of an invention for nucleic acid sequencing using a compacted code technique have been disclosed. While certain embodiments have been described, and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art upon studying this disclosure. In an area of technology such as this, where growth is fast and further advancements are not easily foreseen, the disclosed embodiments may be readily modifiable in arrangement and detail as facilitated by enabling technological advancements without departing from the principles of the present disclosure or the scope of the accompanying claims.

What is claimed is:

1. A method comprising:

a. sequencing a nucleic acid, thereby determining the identity of each base in at least three non-overlapping subsequences of the nucleic acid, each subsequence having ten bases, wherein the second subsequence is between the first and third subsequences;

b. establishing a first format having $4^{10}$ unique seven-byte values, each representing a unique sequence of ten nucleotides;
c. encoding the identity of the first subsequence in the first format;
d. encoding the identity of the second sequence in a second format having one byte;
e. encoding the identity of the third subsequence in the first format; and
f. storing the encoded identity of the first, second, and third subsequences.

2. The method of claim 1, wherein the first subsequence is at a first end of a fragment of the nucleic acid.

3. The method of claim 2, wherein the third subsequence is at a second end of the fragment of the nucleic acid.

* * * * *